(12) United States Patent
Himmelfreundpointner

(10) Patent No.: US 9,119,890 B2
(45) Date of Patent: Sep. 1, 2015

(54) METHOD AND DEVICE FOR INFLUENCING THE SMELL WHICH COMES FROM SHAFT OPENINGS OF UNDERGROUND SEWERS

(71) Applicant: Kurt Himmelfreundpointner, Scharten (AT)

(72) Inventor: Kurt Himmelfreundpointner, Scharten (AT)

( * ) Notice: Subject to any disclaimer, the term of this patent is extended or adjusted under 35 U.S.C. 154(b) by 0 days.

(21) Appl. No.: 14/348,541

(22) PCT Filed: Oct. 5, 2012

(86) PCT No.: PCT/AT2012/000251
§ 371 (c)(1),
(2) Date: Mar. 28, 2014

(87) PCT Pub. No.: WO2013/049867
PCT Pub. Date: Apr. 11, 2013

(65) Prior Publication Data
US 2014/0251127 A1    Sep. 11, 2014

(30) Foreign Application Priority Data

Oct. 5, 2011   (DE) .......................... 10 2011 114 956

(51) Int. Cl.
 *B01F 3/04* (2006.01)
 *B01D 47/06* (2006.01)
(Continued)

(52) U.S. Cl.
CPC ................. *A61L 9/145* (2013.01); *B01D 47/06* (2013.01); *B01D 53/1487* (2013.01); *B01F 3/04056* (2013.01); *B01F 3/04078* (2013.01); *E03F 5/08* (2013.01); *B01D 53/18* (2013.01); *B01D 2252/103* (2013.01); *B01D 2257/90* (2013.01); *B01D 2258/06* (2013.01)

(58) Field of Classification Search
CPC .... B01F 3/04; B01F 3/04007; B01F 3/04049; B01F 3/04056; B01F 3/04078; B01D 47/00; B01D 47/06
USPC .......................................... 95/1, 26, 149, 230
See application file for complete search history.

(56) References Cited

U.S. PATENT DOCUMENTS 4,019,882 A * 4/1977 Herrera ........................... 96/243
6,132,678 A * 10/2000 Heller et al. ...................... 422/4
(Continued)

FOREIGN PATENT DOCUMENTS

EP           0800851 A1   10/1997
GB       1913 05720 A    0/1914
WO    WO 2005/115553 A1  12/2005

OTHER PUBLICATIONS

International Search Report, Feb. 21, 2013, from International Phase of the instant application.
(Continued)

*Primary Examiner* — Robert A Hopkins
(74) *Attorney, Agent, or Firm* — Jackson Patent Law Office

(57) ABSTRACT

The invention relates to a method and device for influencing the smell coming from shaft openings of underground sewers, in which water droplets are sprayed into the air in shafts (1) of underground sewers which are open in the direction of the ambient air.
Said spraying device comprises a pressure vessel (3) containing water and a nozzle (4) having one or more fine openings through which water can escape from the pressure vessel (3), the pressure vessel (3) being subject to a hydrostatic pressure which is by at least 2 bars greater than the ambient pressure, and the diameter of one or more nozzle openings being less than 130 μm.

8 Claims, 1 Drawing Sheet

(51) Int. Cl.
*A61L 9/14* (2006.01)
*E03F 5/08* (2006.01)
*B01D 53/14* (2006.01)
*B01D 53/18* (2006.01)

(56) References Cited

U.S. PATENT DOCUMENTS

| | | | |
|---|---|---|---|
| 6,245,554 B1* | 6/2001 | Durham | 435/266 |
| 6,365,099 B1* | 4/2002 | Castrantas et al. | 422/5 |
| 6,592,813 B1* | 7/2003 | Fox et al. | 422/5 |
| 2004/0096354 A1* | 5/2004 | Nomura et al. | 422/23 |
| 2008/0022709 A1* | 1/2008 | McKee | 62/314 |
| 2009/0010800 A1* | 1/2009 | Resch et al. | 422/4 |
| 2010/0237159 A1* | 9/2010 | Prater et al. | 239/1 |

OTHER PUBLICATIONS

English Translation of the Written Opinion of the International Search Authority, Apr. 5, 2014, from International Phase of the instant application.

English Translation of International Preliminary Report on Patentability Chapter I, Apr. 8, 2014, from International Phase of the instant application.

* cited by examiner

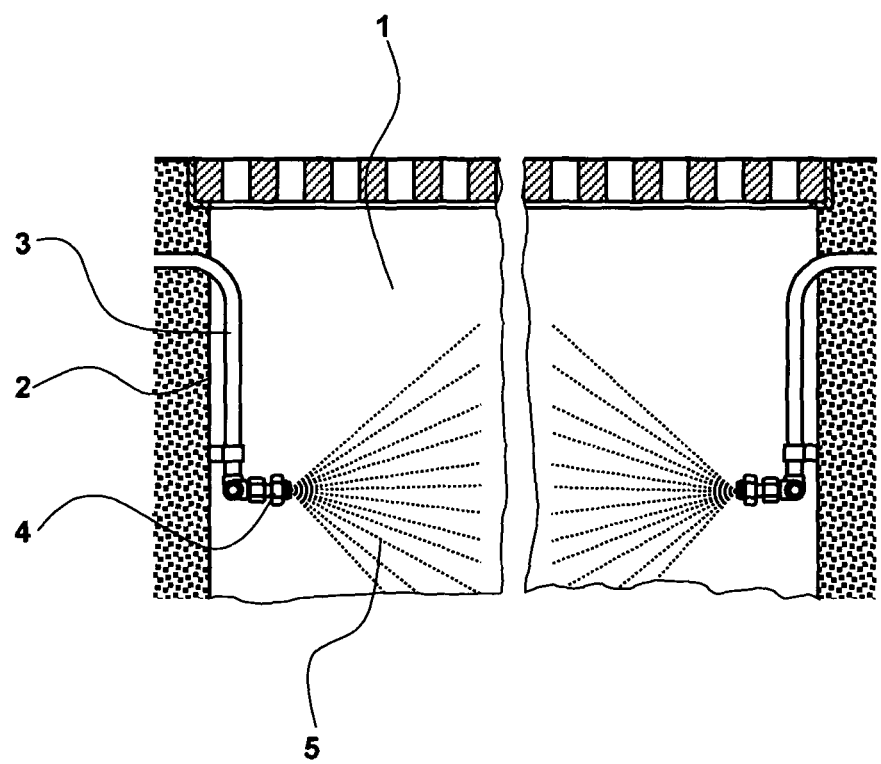

METHOD AND DEVICE FOR INFLUENCING THE SMELL WHICH COMES FROM SHAFT OPENINGS OF UNDERGROUND SEWERS

The invention relates to a method and device for influencing the smell coming from shaft openings of underground sewers.

Sewer vent shafts leading to great heights—typically rooftops—commonly cause a chimney effect due to which air from the underground sewer is conveyed through pipes across the rooftops and air is drawn in by the grated sewer openings on ground level. As with heating systems, the chimney effect may also fail to occur if, e.g., the height is too low and/or the ambient air is much warmer than the air in the chimney due to very hot weather. This may be remedied by integrating blowers in or on sewer systems, preferably in the upward vent pipes. Due to the adverse ambient conditions, the blowers are relatively expensive to buy, maintain and operate.

Another common method is to inject into the sewage, mainly already in collection tanks at large discharge points, microorganisms causing a reduction in the odour formation of the sewage. The weaknesses of this method are that it takes a certain time for the desired effect of the microorganisms to occur in a discharged sewage and that the microorganisms may also be destroyed prematurely by certain compositions of the discharged sewage.

JP 2002360682 proposes to sprinkle the walls of sewage pipes, sewers and underground collection tanks for sewage as well as the shaft entrances to such systems with a powder containing microorganisms capable of dissolving, or even preventing the development of, odour-emitting substances. This method mainly exhibits weaknesses where the smell primarily emanates from the liquid transported in the sewer and not from the sewer walls.

Already in 1913, GB 191305720 A discussed the aim of introducing a larger amount of atmospheric oxygen through a shaft opening of an underground sewer into the sewer and using water sprayed in the shaft for this purpose. In the upper part of the shaft, the cross-section of the shaft is narrowed by a superstructure having a shape similar to the circumferential surface of a truncated cone or pyramid. The narrow section includes a vertically aligned piece of round pipe at the upper end of which a spraying device for water is disposed coaxially to the round pipe. The spraying device comprises a water supply line, a fine opening from which the water sprays downwards in a vertical jet, a pyramid-shaped deflector whose vertically aligned top points upwards and is hit by the jet and a ring in the shape of the circumference of a truncated cone which is narrowed in downward direction and rests on the upper edge of the round pipe. The water jet coming from the line is expanded by the deflector such that it has the shape of a conical circumference. This jet hits the ring in the shape of the circumference of a truncated cone or the inner circumferential surface of the round pipe and is atomised thereon or flows down on it in vertical direction. Optionally, a basket with a granulate which may contain a type of deodorant may be disposed underneath the round pipe, through which the water seeps and drips or flows further down the shaft. Air. Any air present in the shaft comes into intense contact with the sprayed water, is cooled by it and sinks down progressively. Air coming in from above has to flow through said round pipe and will, therefore, necessarily come into heavy contact with the sprayed water.

The operating principle according to GB 191305720 A, which has now been known for almost one hundred years, has not yet been used and has not yet been taken up in the art in order to be used in an improved form. This was presumably discouraged by the evident disadvantages, namely that a high water consumption seems to be necessary, that the sewer shafts are narrowed by the required devices to such a high extent, that maintenance work is rendered difficult or even impossible, and that built-up of ice on the water-sprayed system components is to be expected during winter.

The documents EP1369180 B1, DE19918120 A1, EP802827 B1, DE102004060535 A1, DE102005007805 A1, DE102006044439 A1, DE102007016481 A1, DE102007044272 A1, and DE102007055192 A1 describe nozzles for atomising a liquid into very fine droplets (diameter of less than 0.1 mm). These documents only represent a small exemplary selection from a much larger number of publications describing such nozzles for the finest atomising of liquids. The development of this technology was heavily driven by the application for fuel injection in diesel engines.

The inventor has set himself the task of creating an improved method which can help avoiding odours from sewer systems in the vicinity of their openings. The method to be created is to function in a safe and robust manner and with minimal effort.

In order to solve this task, the principle pursuant to GB 1913/5720 A is used as a basis, according to which water droplets are sprayed into the air in shafts of underground sewers which are open to the ambient air. The proposed improvement thereof according to the invention is to move the water by means of hydrostatic pressure through one or more fine nozzles from a pressure vessel into the environment, the nozzle openings having a diameter of less than 130 micrometers and the hydrostatic pressure being in a range of at least 2 bars.

The invention is illustrated by a drawing:

FIG. 1 shows a somewhat stylised partial sectional side view of the upper part of a sewer shaft equipped according to the invention.

According to FIG. 1, the lines 3 are fitted to the upper part of the walls 2 of a sewer shaft 1, each ending in a nozzle 4. The lines 3 constitute the above-mentioned pressure vessel required by the invention. When supplied with water and pressurised, water is sprayed out of the nozzles 5 and forms a mist 5 consisting of fine droplets.

Due to the inventive design of the nozzles 4 with fine nozzle openings, the size of the sprayed droplets is so small that the droplets exhibit a very large surface in relation to their volume and therefore evaporate very quickly, thus absorbing a large amount of thermal energy from the environment and intensively cooling the ambient air, whereby an inverted chimney effect is achieved, i.e. the air sinks within sewer shaft 1. In addition, molecules and ions contained in the air which lead to odour perception—hereinafter briefly called "odourants"—are bound to water droplets and are thereby at least partially neutralised. Compared to the prior-art design, 1% of the sprayed-in water quantity is sufficient for obtaining the same odour-avoiding effect.

Ideally, the nozzles are disposed as closely as possible to the wall 2 of shaft 1 and directed to the centre of the cross-section of shaft 1 in relation to their spraying direction.

The water flowing from the nozzles 4 does not need to be directed towards a deflector in order to be atomised by it. With the inventive design of the nozzles 4, the water is already atomised into fine droplets. Therefore, only very little water is required and a deflector is not necessary. Not using a deflector results in any corresponding space requirements being omitted and no problems occurring due to ice formation on the deflector or due to erosion of the deflector because of an impinging water jet.

The cross-sectional area of shaft 1 does hardly have to be narrowed by the components to be used according to the inventive design, i.e. lines 3 and nozzles 4, as these components can be disposed directly on the walls 2 of shaft 1.

The orientation of the nozzles 4 does not have to be directed to a deflector as with the prior-art design. This reduces space requirements.

All in all, a much simpler, a much better space-saving construction and a much more robust construction than with the prior-art design of GB 1913/5720 A is therefore possible.

In order to avoid ice formation on the nozzles 4 and lines 3 in a reliable manner, a frost monitor in the form of an ohmic electrical conductor may be fitted to the lines 3 and nozzles 4, which is wound around the lines and nozzles 4 and is heated up by electric current when needed. Such frost monitors are already now typically used as gutter heaters or frost protection for drinking water supply lines and need not be discussed in greater detail herein. The heating requirements may be reduced by sheathing the lines 3 and nozzles 4 (excluding the opening section of the nozzles 4) with a heat-insulating material.

Nozzles 4 which meet the recited requirements have been readily available on the market for some decades and are, for example, constructed in a manner corresponding to the above-mentioned nozzle-related documents.

In general, the effect of the nozzles 4 is better when the sprayed droplets are as small as possible. For example, nozzles are available which can be used at a water pressure with a pressure ratio of 15 bars to spray droplets having an average diameter of 32 µm, with 1.8 to 6 litres of water being sprayed per hour.

Because of widely standardised water system components it is advantageous, especially for economic reasons, to provide for a water pressure of not more than 6 bars. This can be absolutely sufficient.

Preferably, at least one deodorant and/or at least one perfume is added to the water spray. A deodorant as used herein is a chemical or microbiological active agent by which odourants are converted such that they have a less or no disturbing smell. Depending on the agent, this conversion may be achieved by chemical modification or bacterial decomposition. By contrast, a perfume as used herein is a substance which itself has an advantageous odour. Both such active agents—deodorants and perfumes—enhance the effect of the method according to the invention.

It may be beneficial to combine the spraying of liquid with the flow of pressurised air. Compared to the spraying of liquid alone, a finer spraying of the liquid can be achieved at a lower pressure. By atomising the liquid into finer droplets, a quicker local cooling due to evaporation cold as well as the cooling effect caused by the expansion of pressurised air can be achieved at a lower liquid consumption. In some instances, the complexity of equipment may be reduced as lines and fittings do not have to be designed for such high pressures in order to provide the same cooling effect.

Preferably, the spraying device is connected to a control device provided with sensors by which it is switched on or off in response to ambient conditions in the outer surrounding atmosphere and in the sewer atmosphere. Physical parameters deemed to be "ambient conditions" herein typically include temperatures, the flow direction and flow rate of air within the sewer and the concentration of such substances in the ambient air which may be considered indicative of odour. The identification of the optimum switching states for each shaft will certainly mainly be effected empirically. This means that it will become clear, especially with growing experience, which switching state is the optimum for which shaft under which weather condition and which measured concentrations are critical at the relevant points.

Preferably, the control device also switches in response to a schedule. This enables settings to be adjusted proactively, e.g. to typical fluctuations in weather conditions according to the time of day, to weather conditions typical for a particular season and also to loads fluctuating with the activity rhythm of people.

It should be noted that the gas flows generated according to the invention, which are directed via shafts into a sewer system, will also cause gas flows out of the sewer system due to the displacement of gas in the sewer system at one or several points. Therefore, with the inventive design of a sewer system, an appropriate number of sufficiently close exhaust openings for displaced gas from the sewer system should also be provided, and these openings should be located in places where odours are not a nuisance.

For clarification, the term "shaft" as used herein is not only meant to refer to a vertical sewer access which can be closed with a cover at the top, but generally also to sloping inlets into a sewer system.

Of course, the invention is particularly valuable when used at such inlets which are traditionally considered as a "shaft". However, advantages also arise with smaller and non-vertical sloping inlets into a sewer system if such inlets are not completely sealed from ambient air in their upper longitudinal section.

The invention claimed is:

1. A method for avoiding odour from a sewer system in the vicinity of a vertical shaft of the sewer system which is open to the ambient air, the method comprising:
    generating a flow of air into the sewer system by spraying water droplets into an upper part of the vertical shaft, the spraying step including moving water by hydrostatic pressure through a fine nozzle from a pressure vessel and into the shaft, the pressure in the pressure vessel being at least 2 bars and a nozzle opening having a diameter of less than 130 micrometers, thereby cooling the air and causing the air to sink within the vertical shaft.

2. A method according to claim 1 wherein the water is sprayed together with a deodorant added thereto or a perfume added thereto.

3. A method according to claim 1 wherein the spraying process is adjusted by a controller which performs the setting of the spraying process in response to ambient conditions detected by sensors.

4. A method according to claim 1 wherein the spraying process is adjusted by a controller which performs the setting of the spraying process in response to a schedule.

5. A method according to claim 1 wherein the step of spaying water droplets includes spaying water droplets under a sewer grate of the sewer system.

6. A sewer system comprising:
    a vertical shaft which is open to the ambient air, the vertical shaft including an upper part; and
    a spraying device disposed in the upper part of the vertical shaft, the spraying device being configured to spray water droplets into the upper part of the shaft, the spraying device comprising a pressure vessel containing water and a nozzle having a fine opening through which water can escape from the pressure vessel, the pressure vessel being subject to a hydrostatic pressure which is by at least 2 bars greater than the ambient pressure, and the diameter of a nozzle opening being less than 130 µm, the spraying device thereby generating a flow of air into the sewer system by cooling the air and causing the air to sink within the vertical shaft, wherein a nozzle is positioned on a wall of the shaft, and its spraying direction is directed to the centre of the cross-sectional area of the shaft.

7. A device for avoiding odour from a sewer system in the vicinity of a shaft of the sewer system which is open to the ambient air, wherein a spraying device is disposed in the shaft which is capable of spraying water droplets into the air in the shaft, characterised in that the spraying device comprises a pressure vessel containing water and a nozzle having a fine opening through which water can escape from the pressure vessel, the pressure vessel being subject to a hydrostatic pressure which is by at least 2 bars greater than the ambient pressure, and the diameter of a nozzle opening being less than 130 μm, and the pressure vessel and nozzle are provided with a heat-insulating jacket.

8. A device for avoiding odour from a sewer system in the vicinity of a shaft of the sewer system which is open to the ambient air, wherein a spraying device is disposed in the shaft which is capable of spraying water droplets into the air in the shaft, characterised in that the spraying device comprises a pressure vessel containing water and a nozzle having a fine opening through which water can escape from the pressure vessel, the pressure vessel being subject to a hydrostatic pressure which is by at least 2 bars greater than the ambient pressure, and the diameter of a nozzle opening being less than 130 μm, and the pressure vessel and nozzle are provided with a heating device acting as a frost monitor.

* * * * *